United States Patent [19]

Capiris et al.

[11] Patent Number: 5,086,064
[45] Date of Patent: Feb. 4, 1992

[54] 3,5-DI-TERTIARY-BUTYL-4-HYDROXYPHENYL THIAZOLYL, OXAZOLYL, AND IMIDAZOLYL METHANONES AND RELATED COMPOUNDS AS ANTIINFLAMMATORY AGENTS

[75] Inventors: Thomas Capiris, Plymouth; David T. Connor; Jagadish C. Sircar, both of Ann Arbor, all of Mich.

[73] Assignee: Warner-Lambert Company, Morris Plains, N.J.

[21] Appl. No.: 646,411

[22] Filed: Jan. 31, 1991

Related U.S. Application Data

[63] Continuation-in-part of Ser. No. 500,175, Mar. 27, 1990, abandoned.

[51] Int. Cl.$^5$ ................ C07D 277/24; C07D 275/02; A61K 31/425
[52] U.S. Cl. .................................. 514/365; 514/372; 518/200; 518/201; 518/214; 518/236; 518/248; 518/343; 518/378
[58] Field of Search ............ 548/200, 214, 201; 514/365, 372

[56] References Cited

U.S. PATENT DOCUMENTS 4,535,165  8/1985  Moore ................... 548/204

FOREIGN PATENT DOCUMENTS 0059090  9/1982  European Pat. Off. .
0189771  8/1986  European Pat. Off. .
0269981  6/1988  European Pat. Off. .

OTHER PUBLICATIONS

Mar., Advanced Organic Chemistry, pp. 484–486, (1985).

*Primary Examiner*—Robert Gerstl
*Attorney, Agent, or Firm*—Joan Thierstein

[57] ABSTRACT

The novel 3,5-di-tertiary-butyl-4-hydroxyphenylthiazolyl, -oxazolyl, or -imidazolyl methanones and methanone oximes of the present invention are antiinflammatory agents having activity as inhibitors of 5-lipoxygenase, cyclooxygenase or both.

11 Claims, No Drawings

3,5-DI-TERTIARY-BUTYL-4-HYDROXYPHENYL THIAZOLYL, OXAZOLYL, AND IMIDAZOLYL METHANONES AND RELATED COMPOUNDS AS ANTIINFLAMMATORY AGENTS

This is a continuation-in-part of U.S. application Ser. No. 07/500,175, filed Mar. 27, 1990, now pending.

BACKGROUND OF THE INVENTION 3,5-Di-tertiary-butyl-4-hydroxyphenyl is disclosed as a moiety in a variety of compounds.

For example, copending U.S. application Ser. No. 395,165 discloses the moiety in its styryl pyrazoles, isoxazoles, isothiazoles, or imidazoles. However, the present compounds differ from this disclosure by the methanone group or the methanone oxime between the 3,5-di-tertiary-4-hydroxyphenyl and each of a thiazolyl, oxazolyl or imidazolyl ring.

Other references disclose compounds combining a 3,5-di-tertiary-butyl-4-hydroxyphenyl with various other rings such as thiadiazoles, oxadiazoles or triazoles. See copending U.S. application Ser. No. 07/426,814, which further cites other such combinations. J6 3239-273-A, described in Derwent Abstract Number 88-326016/46, includes an imidazole and phenyl (optionally substituted) bridged by methylene or carbonyl. EP 241-043A shows thiazolyl, oxazolyl, and imidazolyl and phenyl (optionally substituted) bridged by various alkylenyl or alkenylenyl chains interrupted by a C(Z) group where Z is O, S, NOR$_3$ or NH. An oxazole or imidazole ring is attached by a bond to 3,5-di-tert-butyl-4-hydroxyphenyl in J5 8148-858-A, described in Derwent Abstract Number 83-786513/41, or by CO or CHR$_5$ in EP24-829 of Derwent Abstract Number 19743 D/12.

However, such references differ from the present invention in both the heteroaryl ring moiety and the substituent between the heteroaryl ring and the 3,5-di-tertiary-butyl-4-hydroxyphenyl moiety. The present invention is limited to rings having two heteroatoms and a methanone or methanone oxime between the rings.

Finally, a very broad generic disclosure relating a heteroaryl and various bridging groups to a phenyl not including a 3,5-di-tert-butyl-4-hydroxyphenyl is shown in EP 274-867A of Derwent Abstract Number 88-199351-29.

SUMMARY OF THE INVENTION

The present invention is a novel compound of the formula (I)

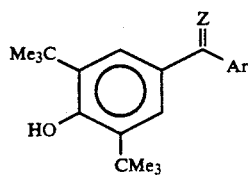

and a pharmaceutically acceptable base or acid addition salt thereof; in which
Z is O, NOH or NOCH$_3$;
Ar is

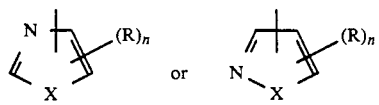

wherein
X is NR$_1$, O, or S;
R is independently hydrogen, lower alkyl, halogen, CO$_2$R$_2$, or

wherein R$_1$ is hydrogen or lower alkyl, R$_2$ and R$_3$ are independently hydrogen or lower alkyl; and n is an integer of one or two with the proviso that when n is two than R cannot be CO$_2$R$_2$ or

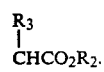

The present invention is also a pharmaceutical composition for treating a disease or condition, such as rheumatoid arthritis, osteoarthritis, other inflammatory conditions, psoriasis, allergic diseases, inflammatory bowel disease, GI ulcers, cardiovascular conditions including ischemic heart disease and atherosclerosis, and ischemia-induced cell damage, particularly brain damage caused by stroke, preferably an inflammatory disease or condition, comprising an antiinflammatory, antipsoriatic, antiallergy, antiulcer, or antiischemic, antiatherosclerotic, or cytoprotective amount of the compound of the formula I or a pharmaceutically acceptable salt thereof as defined above and a pharmaceutically acceptable carrier.

The present invention is also a method of treating a disease or condition as noted above in a mammal, particularly a human, suffering therefrom which comprises administering a compound of the formula I or salt thereof as defined above in unit dosage form.

The invention also provides for use of any such compound of formula I or salt thereof in the manufacture of a medical therapeutic agent.

The pharmaceutical composition or method of treating which is the present invention is meant to include what is understood to be prophylactic to one of a foregoing named disease or condition.

The compounds of the formula I have activity as inhibitors of 5-lipoxygenase, cyclooxygenase or both to provide the use for the pharmaceutical composition and methods of the present invention.

The preferred compounds of the formula I are
[3,5-Bis(1,1-dimethylethyl)-4-hydroxyphenyl](5-methyl-3-isoxazolyl)methanone,
[3,5-Bis(1,1-dimethylethyl)-4-hydroxyphenyl]-2-thiazolylmethanone, and
[3,5-Bis(1,1-dimethylethyl)-4-hydroxyphenyl](5-methyl-3-isoxazolyl)methanone, O-methyloxime.
More preferred compounds are
[3,5-Bis(1,1-dimethylethyl)-4-hydroxyphenyl]-2-thiazolylmethanone and
[3,5-Bis(1,1-dimethylethyl)-4-hydroxyphenyl](5-methyl-3-isoxazolyl)methanone, O-methyloxime.
The most preferred compound is

[3,5-Bis(1,1-dimethylethyl)-4-hydroxyphenyl]-2-thiazolylmethanone.

A DETAILED DESCRIPTION OF THE INVENTION

In the present invention "lower alkyl is alkyl of from one to six carbons, inclusive, and means methyl, ethyl, propyl, butyl, pentyl, or hexyl and isomers thereof.

Halogen is chloro, iodo, bromo or fluoro.

Me is methyl.

The compounds of the invention may contain geometric or optical isomers. Thus, the invention includes the individual isomers and mixtures thereof. The individual isomers may be prepared or isolated by methods known in the art.

The compounds of the invention may contain an asymmetric carbon atom, particularly, for example, at the R substituent of the compound of formula I, which is $CHR_3CO_2R_2$. Thus, the invention includes individual enantiomers, the pure S, the pure R isomer, and mixtures thereof. The individual enantiomers may be prepared or isolated by methods known in the art. Likewise diastereomers are included in the invention, if possible, both as individuals or mixtures thereof.

A tautomeric form of selected compounds of formula I would be recognized by an ordinarily skilled artisan to be within the present invention.

The compounds of formula I are useful both in the free base and where possible the free acid form of in the form of base salts thereof, as well as in the form of acid addition salts. All forms are within the scope of the invention. In practice, use of the salt form amounts to use of the acid or free base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the information of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases for a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, and triethanolamine; amino acids such as arginine, and lysine; choline; guanidine; N-methylglucosamine; N-methylpiperazine; morpholine; ethylenediamine; N-benzylphenethylamine; tris(-hydroxymethyl) aminomethane; and the like. (See, for example, "Pharmaceutical Salts," *J. Pharm. Sci.*, 66(1), 1–19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The base salts of compounds of formula I described above are prepared by reacting the appropriate base with a stoichiometric equivalent of the acid compounds of formula I to obtain pharmacologically acceptable base salts thereof.

The acid solution salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution. The base salts of compounds of formula I described above are prepared by reacting the appropriate base with a stoichiometric equivalent of the acid compounds of formula I to obtain pharmaceutically acceptable base salts thereof.

The acid solution salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may also exist in hydrated or solvated forms. Again, in practice, use of any of these forms amounts to the free base or acid form.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2 \times 10^6$ cells/mL. Cells are incubated with and without test agent (in DMSO) (1% DMSO is without effect on arachidonic acid metabolism) for 10 minutes at room temperature. Calcium ionophore A23187 (5 μM) is added and cells are incubated for 7 minutes at 37° C. The reaction is stopped by chilling the tubes on ice for 10 minutes. Cells are separated by centrifugation and the supernatant is stored at $-20°$ C. Aliquots (100 μL) are analyzed for $LTB_4$ and $PGF_{2\alpha}$ using radioimmunoassay kits as provided by the supplier.

Table I contains biochemical data obtained from this whole cell assay as $IC_{50}$s which are calculated as the amount of test compound causing 50% inhibition or % of inhibition at the named micromoles (μM) of LTB14 or $PGF_{2\alpha}$ formaton.

Carrageenan-Induced Rat Foot Paw Edema-2 (CFE-2) Assay: Protocol

Carageenan solution (1% w/v) is prepared by dissolving 100 mg carrageenan (Marine Colloidal Div., Springfield, N.J.) in 10 mL of sterile saline (0.9%) solution (Travenol). The solution is vortexed for 30 to 45 minutes. Animals are dosed with compound 1 hour before carrageenan challenge. Foot paw edema is induced by injecting 0.10 mL of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured 5 hours after carrageenan. The difference between the 5-hour and the initial paw volume is expressed as delta edema. The delta edema for each test group of animals is used to calculate the percent inhibition of edema achieved by the compound at the test dose compared with the vehicle control group. The data in Table I (the dose at which swelling is inhibited by the noted percent) is calculated by probit analysis for the dose at which percent inhibition occurs.

TABLE I

[Structure: 3,5-di-tert-butyl-4-hydroxyphenyl ketone with Ar group]

$Me_3C$ and $CMe_3$ substituents on phenol ring, HO group, C(=O)Ar group

| Example Number | Ar | Z | ARBL $IC_{50}$ (μM) | ARBC $IC_{50}$ (μM) | CFE |
|---|---|---|---|---|---|
| 1 | [isoxazole-CH₃] | O | $0.83^a$ | $0.06^c$ | 37% @ 3 mg/kg |
| 4 | [thiazole] | O | $91\%^b$ @ 10 | $91\%^d$ @ 10 | |
| 11 | [thiazole] | NOH | N @ $10^b$ | N @ $10^d$ | |
| 14 | [isoxazole-CH₃] | $NOCH_3$ | $100\%^b$ @ 10 | $97\%^d$ @ 10 | |

$^a IC_{50}$ for $LTB_4$ inhibition.
$^b$Percent inhibition of $LTB_4$ @ 10 μM (N means not active at the dose tested).
$^c IC_{50}$ for $PGF_{2\alpha}$.
$^d$Percent inhibition of $PGF_{2\alpha}$ @ 10 μM (N means not active at the dose tested).

Accordingly, the present invention also includes a pharmaceutical composition for treating one of the above diseases or conditions comprising an antidisease or anticondition effective amount of a compound of the formula I or salt thereof as defined above together with a pharmaceutically acceptable carrier.

The present invention further includes a method for treating one of the above named diseases or conditions in mammals, including man, suffering therefrom comprising administering to such mammals either orally or parenterally, preferably oral, a corresponding pharmaceutical composition containing compounds of the formula I or salt thereof.

A physician or veterinarian of ordinary skill readily determines a subject who is exhibiting symptoms of any one or more of the diseases described above. Regardless of the route of administration selected, the compounds of the present invention of the formula I as described in pharmaceutical compositions above are formulated into pharmaceutically acceptable dosage forms by conventional methods known to the pharmaceutical art.

The compounds can be administered in such oral unit dosage forms as tablets, capsules, pills, powders, or granules. They also may be administered rectally or vaginally in such forms as suppositories or bougies; they may also be introduced parenterally (e.g., subcutaneously, intravenously, or intramuscularly) using forms known to the pharmaceutical art. They are also introduced directly to an affected area (e.g., in the form of eye drops or by inhalation). For the treatment of asthma or allergies, particularly dermatological disorders such as erythema, psoriasis, and acne the compounds may also be administered topically in the form of ointments, gels, or the like. However, in general, the preferred route of administration is oral.

An effective but nontoxic quantity of the compound is employed in treatment. The ordinarily skilled physician or veterinarian will readily determine and prescribe the effective amount of the compound to prevent or arrest the progress of the condition for which treatment is administered. In so proceeding, the physician or veterinarian could employe relatively low dosages at first, subsequently increasing the dose until a maximum response is obtained.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula (I) or pharmacologically acceptable salt thereof to achieve a therapeutic effect will, of course, vary both with the particular compound, the route of administration, the mammal under treatment, and the particular disorder or disease concerned. A suitable dose of a compound of formula (I) or pharmacologically acceptable salt thereof for a mammal suffering from, or likely to suffer from any condition as described hereinbefore is 0.1 μg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range of 0.1 ng to 100 μg of the compound per kilogram, typically about 0.1 μg/kg.

In the case of oral dosing for the treatment of prophylaxis of arthritis or inflammation in general, due to any course, a suitable dose of a compound of formula (I) or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferably to present it as a pharmaceutical formulation comprising a compound of formula (I) or a pharmacologically acceptable acid addition or base salt thereof and a pharmacologically acceptable carrier therefor. Such formulations constitute a further feature of the present invention.

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combustions of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprofen aluminum, indoprofen, ketoprofen, naproxen, benoxaprofen flurbiprofen, fenoprofen, fenbufen, pirprofen, carprofen, oxaprizin, pranoprofen, microprofen, tioxaprofen, suprofen, alminoprofen, tiaprofen, fluprofen, and bucloxic acid. Structurally related propionic acid derivatives having similar analgsic and antiinflammatory properties are also intended to be included in this group.

Thus, "propionic acid derivatives" as defined herein are nonnarcotic analgesics/nonsteroidal antiinflammatory drugs having a free —CH(CH₃)COOH or —CH₂CH₂COOH group (which optionally can be in the form of a pharmaceutically acceptable salt group, e.g., —CH(CH₃)COO⁻NA⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zompirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein an nonnarcotic analgesics/nonsteroidal antiinflammatory drugs having a free —CH₂COOH group (which optionally can be in the form of a pharmaceutically acceptable salt group, e.g., —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

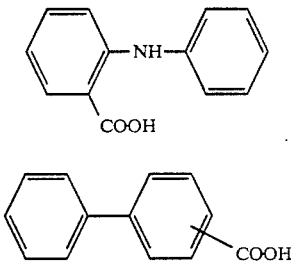

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

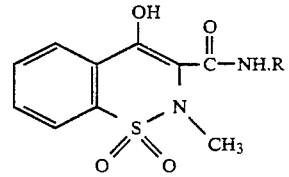

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiiflammatory properties are also intended to be encompassed by this group.

Thus, "oxicams" as defined herein are nonnarcotic analgesics/nonsteroidal antiinflammatory drugs which have the general formula:

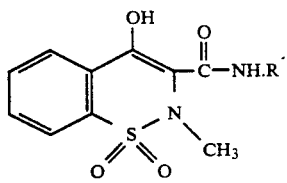

wherein R is an aryl or heteroaryl ring system.

The following NSAIDs may also be used: acematacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirazole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidine, pirprofen, pranoprofen, proglumetacin, maleate, proquazone, pyridoxiprofen, sodoxicam, suprofen, talmetacin, talniflumate, tenoxicam, thiazolinobutazone, thielavin B, tiaprofenic acid, tiaramide HCl, tiflamizole, timegadine, toxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the formula I are prepared generally by the following processes and constitute a further aspect of the present invention.

Generally, the compounds of formula I are prepared by one of the following methods A:, B: or C: and shown hereinafter in Schemes I, II, or III, respectively.

SCHEME I
Method A

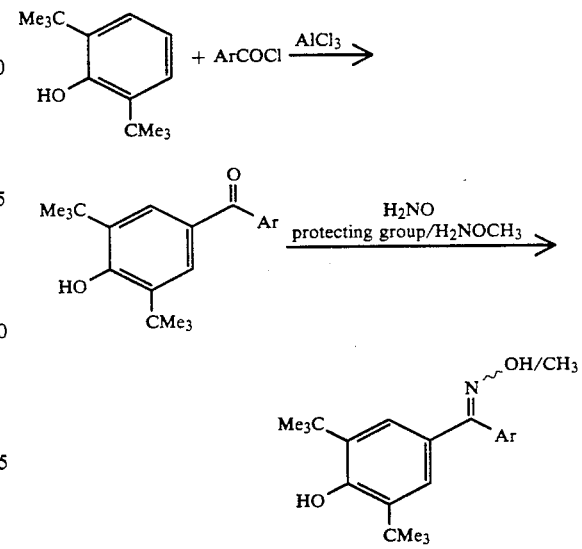

SCHEME II
Method B

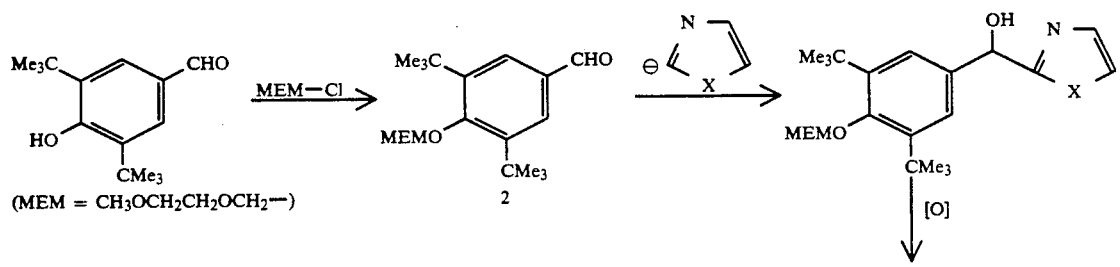

-continued
SCHEME II
Method B

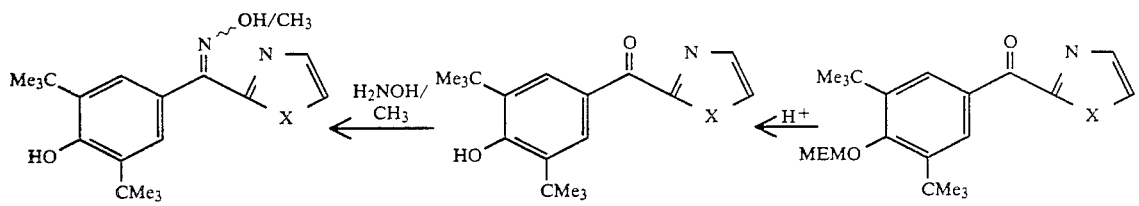

Scheme III
Method C

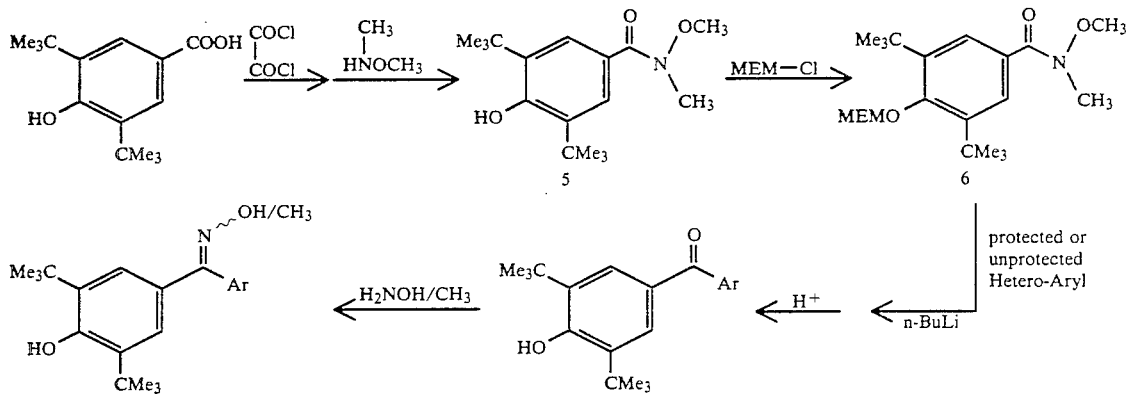

General Procedures for the Synthesis of 3,5-Di-tert-butyl-4-hydroxyphenyl Thiazolyl, Oxazolyl, and Imidazolyl Methanones The target compounds are prepared by three different methods. One method, shown in Scheme I above, involves a Friedel-Crafts reaction. 2,6-Di-tert-butylphenol is reacted with the acid chloride at $-10°$ C. to $+20°$ C. in the presence of a Lewis acid such as $AlCl_3$, $TiCl_4$, or others in solvents like $CS_2$, 1,2-dichloroethane, and $CCl_4$ for 1 hour to 24 hours. The products are isolated by the standard procedures known in the art and flash chromatographed to purify. Another method shown in Scheme II above involves anion chemistry. 3,5-Di-tert-butyl-4-[(2-methoxyethoxy)methoxy]benzaldehyde is reacted with slight excess of anion of the heterocyclic compound at $-78°$ C. to $+10°$ C. for 1 hour to 20 hours in solvents like THF or ether. The products are isolated by the techniques known in the art and, if necessary, purified by flash chromatography. The intermediate carbinol is oxidized by $KMnO_4$ in the presence of tris[2-(2-methoxethoxy)ethyl]amine in solvents like methylene chloride, chloroform, or carbon tetrachloride at $24°$ C. for 0.25 hours to 4.0 hours. The isolated product is deprotected using 1% to 10% HCl/MeOH at $24°$ C. for 0.25 hour to 3 days. Finally, a method shown in Scheme III also uses anion chemistry. 3,5-Di-tert-butyl-4-hydroxybenzoylchloride is converted to the corresponding N,O-dimethylhydroxamate by reacting with N,O-dimethylhydroxylamine.HCl and a base such as N-methylpiperidine, triethylamine, or diisopropylamine in solvents such as $CH_2Cl_2$, $CHCl_3$, $Et_2O$ or other organic solvent for 1 to 20 hours. The N,O-dimethylhydroxamide is then reacted with 2-methoxyethoxymethyl chloride and 1 to 3 equivalents of diisopropylethylamine in solvent such as $CH_2Cl_2$, $CHCl_3$ or $Et_2O$ for 24 to 96 hours at reflux temperature. The protected N,O-dimethylhydroxamate is reacted with the anion of the heterocyclic compounds at $-78°$ C. to $25°$ C. in solvents such as $Et_2O$ or THF for 1 to 4 hours. The reaction mixture is worked up as known in the art and purified by flash chromatography. The product is deprotected with 1 to 10% HCl/MeOH for 0.25 to 3 days at $24°$ C. to give the final product.

One of skill in the art would recognize variations in the sequence and would recognize variations in the appropriate reaction conditions from the analogous reactions shown or otherwise known which may be appropriately used in the processes above to make the compounds of the formula I herein.

Introduction and removal of such suitable oxygen protecting groups are well known in the art of organic chemistry; see for example, "Protective Groups in Organic Chemistry", J. F. W. McOmie, ed., (New York, 1973), pages 43ff, 95ff, J. F. W. McOmie, Advances in Organic Chemistry, Vol. 3, 159-190 (1963); J. F. W. McOmie, Chem. & Ind., 603 (1979); and T. W. Greene, "Protective Groups in Organic Synthesis", Wiley (New York), 1981, Chapters 2, 3 and 7.

Examples of suitable oxygen protecting groups are benzyl, trialkylsilyl, ethoxyethyl, methoxyethoxymethyl, methoxymethyl, trialkylsilylethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

The products of the reactions described herein are isolated by conventional means such as extraction, distillation, chromatography, and the like.

Starting materials not described herein are available commercially, are known, or can be prepared by methods known in the art.

The salts of the compounds of formula I described above are prepared by reacting the appropriate base r acid with a stoichiometric equivalent of the compounds of formula I.

The invention is further elaborated by the representative examples as follows. Such examples are not meant to be limiting.

EXAMPLE 1

[3,5-Bis(1,1-dimethylethyl)-4-hydroxyphenyl](5-methyl-3-isoxazolyl)methanone

To a solution of 20.6 g (0.1 mole) of 2,6-di-tert-butylphenol and 15.6 g (0.107 mole) of 5-methylisoxazole-3-carboxylic acid chloride in 100 mL of $CS_2$ is added 14.3 g (0.107 mole) of $AlCl_3$ at $+5°$ C. Vigorous stirring is maintained at that temperature for 1 hour and then at room temperature for 1 hour. The $CS_2$ is decanted off and the residue treated with 350 mL of ice cold 1N HCl and extracted with $Et_2O$. The extracts are washed with saturated $NaHCO_3$ solution and brine, dried with $Na_2SO_4$ and evaporated to give a mixture of products. The desired product is separated by flash chromatography (0% to 50% $CH_2Cl_2$/n-hexane) on silica gel to give 4.4 g of the crude ketone which is recrystallized from n-pentane to give 2.3 g (14%) of pale yellow crystals, [3,5-bis(1,1-dimethylethyl)-4-hydroxyphenyl(5-methyl-3-isoxazolyl)methanone, mp 120° C.; $^1$H NMR (CDCl$_3$) δ 1.48 (s, 18H, tert-butyl), 2.52 (s, 3H, CH$_3$), 5.85 (s, 1H, OH), 6.48 (s, 1H, isoxazole aromatic), 8.23 (s, 2H, phenyl aromatics); IR (KBr) 1590, 1600, 1650, 3600 cm$^{-1}$; MS (DEI) m/e 315 (M+), 300 (M-CH$_3$).

Anal. for $C_{19}H_{25}NO_3$: Calcd: C, 72.35; H, 7.99; N, 4.44. Found: C, 71.96; H, 8.08; N, 4.34.

EXAMPLE 2

3,5-Bis(1,1-dimethylethyl)-4-[(2-methoxyethoxy)methoxy]benzaldehyde

A mixture of 11.7 g (0.05 mole) of 3,5-di-tert-butyl-4-hydroxybenzaldehyde and 19.4 g (0.15 mole) of diisopropylethylamine in 150 mL of $CH_2Cl_2$ is treated with 18.7 g (0.15 mole) of 2-methoxyethoxymethyl chloride (MEM-Cl) and the resulting solution is heated under reflux for 48 hours and evaporated to dryness. The residue is taken up in $CH_2Cl_2$, washed with 1N HCl and brine, and dried with MgSO$_4$. The solution is evaporated and the residue is filtered through flash grade silica gel, washing with 1:1 $CH_2Cl_2$/n-hexane. Evaporation gives a tan oil, 12.2 g of 3,5-bis(1,1-dimethylethyl)-4-[(2-methoxyethoxy)methoxy]benzaldehyde (76%) which is used without further purification.

β$^1$H NMR (CDCl$_3$) δ 1.4 (s, 18H, tert-butyl), 3.3 (s, 3H, CH$_3$), 3.5 (m, 2H, CH$_2$), 3.8 (m, 2H, CH$_2$), 4.9 (s, 2H, OCH$_2$O), 7.7 (s, 2H, aromatics), 9.8 (s, 1H, CHO).

Anal. for $C_{19}H_{30}O_4$: Calcd: C, 70.77; H, 9.38. Found: C, 70.87; H, 9.33.

EXAMPLE 3

[3,5-Bis(1,1-dimethylethyl)-4-hydroxyphenyl](1-methyl-1H-imidazol-2-yl)methanone To a solution of 1.67 g (0.0165 mole) of diisopropylamine in 100 mL THF is added 10.3 mL of a 1.6M n-BuLi/hexane solution (0.0165 mole) at $-78°$ C. After 15 minutes at that temperature 1.31 g (0.016 mole) of 1-methylimidazole is slowly added and the reaction mixture is warmed to $+10°$ C. and then recooled. The MEM-protected aldehyde from Example 2 (4.6 g, 0.0143 mole) in 25 mL THF is added and the reaction mixture is allowed to remain at room temperature for 17 hours. The reaction mixture is poured into 350 mL of ice cold 0.5N HCl and extracted with $CH_2Cl_2$. The extracts are washed with saturated NaHCO$_3$ and brine, dried with Na$_2$SO$_4$, and evaporated. The residue is recrystallized from $Et_2O$ - n-hexane to give 3.85 g of a white solid intermediate carbinol, mp 134°–136° C.

Anal. for $C_{23}H_{36}N_2O_4$: Calcd: C, 68.28; H, 8.97; N, 6.93. Found: C, 68.18; H, 8.91; N, 6.83.

A solution of 405 mg (0.001 mole) of this intermediate and 32.3 mg (0.0001 mole) of (tris[2-(2-methoxyethoxy)ethyl]amine in 20 mL of $CH_2Cl_2$ at room temperature is treated over a 5-minute period with 316 mg (0.002 mole) of powdered KMnO$_4$. The mixture is stirred 2 hours, filtered through celite, and evaporated to give 0.4 g of a yellow oil, IR (film) 1645 cm$^{-1}$.

The yellow oil is dissolved in 25 mL of 5% (w/v) HCl/MeOH, allowed to stand at room temperature for 24 hours, and evaporated. The residue is recrystallized from EtOAc-iPr$_2$O to give a white crystalline hydrochloride. Loss of hydrogen chloride accompanies drying at 110° C. under high vacuum to give 125 mg of [3,5-bis(1,1-dimethylethyl)-4-hydroxyphenyl](1-methyl-1H-imidazol-2-yl)methanone, mp 172°–174° C. (24% overall yield).

$^1$H NMR (DMSO-d$_6$) δ 1.42 (s, 18H, tert-butyl), 3.95 (s, 3H, NCH$_3$), 7.18 (s, 1H, OH), 7.52 (s, 1H, imidazole aromatic), 7.83 (s, 1H, imidazole aromatic), 8.23 (s, 2H, phenyl aromatic); IR (KBr) 1580, 1630 cm$^{-1}$; MS (DEI) m/e 314 (M+), 299 (M-CH$_3$).

Anal. for $C_{19}N_{26}N_2O_2$: Calcd: C, 72.58; H, 8.34; N, 8.91. Found: C, 72.19; H, 8.23; N, 8.53.

EXAMPLE 4

[3,5-Bis(1,1-dimethylethyl)-4-hydroxyphenyl]-2-thiazolylmethanone

The compound in this example is prepared starting from the compound is Example 2 and thiazole according to the method reported for Example 3. There is obtained 1.17 g (29% overall yield) yellowish-white crystals, [3,5-bis(1,1-dimethylethyl)-4-hydroxyphenyl]-2-thiazolymethanone, mp 106°–108.5° C.; $^1$H NMR (CDCl$_3$) δ 1.49 (s, 18H, tert-butyl), 5.83 (s, 1H, OH, 7.66 (d, J=3.15, 1H, thiazole aromatic), 8.06 (d, J=3.07, 1H, thiazole aromatic), 8.48 (s, 2H, phenyl aromatics); IR (KBr) 1480, 1593, 1639, 3602 cm$^{-1}$; MS (DEI) m/e 317 (M+), 302.

Anal. for $C_{18}H_{23}NSO_2$: Calcd: C, 68.12; H, 7.31; N, 4.41; S, 10.10. Found: C, 68.21; H, 7.34; N, 4.40; S, 10.13.

EXAMPLE 5

N-Methoxy-N-methyl-(3,5-di-tert-butyl-4-hydroxy)-benzamide

A solution of 62.6 g (0.25 mole) of 3,5-di-tert-butyl-4-hydroxybenzoic acid in 500 ml $CH_2Cl_2$ is treated with 66.19 g (0.527 mole) of oxalyl chloride and four drops of DMF. After stirring at room temperature for 16 hours the reaction mixture is evaporated to yield a yellow solid which is dissolved in 200 pl mL of $CH_2Cl_2$. This solution is added, over a period of 25 minutes, to a solution of 64 g (0.645 mole) of N-methylpiperidine and 31.6 g (0.324 mole) of N,O-dimethylhydroxylamine hydrochloride in 400 mL of $CH_2Cl_2$ while the temperature is maintained at +5° to 10° C. The reaction mixture is stirred at room temperature for 16 hours and then poured into 500 mL of ice cold 5% $Na_2CO_3$. The $CH_2Cl_2$ layer is washed with 5% $Na_2CO_3$, 3N HCl and brine, dried with $Na_2SO_4$, and evaporated to yield a yellow solid. Recrystallization from n-hexane gives off-white crystals, N-methoxy-N-methyl-(3,5-di-tert-butyl-4-hydroxy)benzamide, 60.8 g (83%), mp 112°–113.5° C.; $^1$H NMR (CDCl$_3$) δ 1.45 (s, 18H, tert-buytl), 3.34 (s, 3H, NCH$_3$), 3.63 (s, 3H, OCH$_3$), 5.49 (s, 1H, OH), 7.57 (s, 2H, aromatics).

Anal. for $C_{17}H_{27}NO_3$: Calcd: C, 69.59; H, 9.28; N, 4.77. Found: C, 69.71; H, 9.61; N, 4.56.

EXAMPLE 6

N-Methoxy-N-methyl-[3,5-di-tert-butyl-4-[(2-methoxyethoxy)methoxy]]benzamide

This compound is prepared from the compound in Example 5 according to the method reported for the compound in Example 2. It is obtained as an amber oil in 50% yield of N-methoxy-N-methyl-[3,5-di-tert-butyl4[(2-methoxyethoxy)methoxy]]benzamide, and is used without further purification. $^1$H NMR (CDCl$_3$) δ 1.44 (s, 18H, tert-butyl), 3.35 (s, 3H, C—OCH$_3$), 3.43 (s, 3H, NCH$_3$), 3.61 (s, 3H, NOCH$_3$), 3.63–3.70 (m, 2H, CH$_2$), 3.97–4.00 (m, 2H, CH$_2$), 5.00 (s, 2H, OCH$_2$O), 7.60 (s, 2H, aromatics).

Anal. for $C_{21}H_{35}NO_5$: Calcd: C, 66.11; H, 9.25; N, 3.67. Found: C, 66.08; H, 9.28; N, 3.35.

EXAMPLE 7

[3,5-bis(1,1-dimethylethyl)-4-hydroxyphenyl](5-chloro-1,3-dimethyl-1H-pyrazol-4-yl)methoanone 4-Bromo-5-chloro-1,3-dimethylpyrazole (Butler, D. E., DeWald, H. A., J. Org. Chem., 1971, 36, 2545) (6.3 g, 0.03 mole) in Et$_2$O (100 mL) is cooled in +10° C. and treated rapidly (25 seconds) with 1.6M n-butyllithium (20 mL). After stirring while suspension at room temperature for 15 minutes it is added, all at once, to a solution of N-methoxy-N-methyl-[3,5-di-tert-butyl-4[(2-methoxyethoxy)methoxy] benzamide (Example 6) (11.43 g, 0.03 mole) in Et$_2$O (100 mL ) at −70° C. The reaction mixture is stirred at room temperature for 16 hours and then treated with 220 mL ice cold 0.4N HCl. The Et$_2$O layer is washed with saturated NaHCO$_3$, dried with Na$_2$SO$_4$ and evaporated to give an amber oil which is allowed to stand for 3 days in 100 mL 5% (w/v) HCl/MeOH. Evaporation yields an oil which is taken up to Et$_2$O, washed with saturated NaHCO$_3$ and brine, dried with Na$_2$SO$_4$ and evaporated The residue is purified by flash chromatography (0–25% EtOAc/CH$_2$Cl$_2$) on silica gel to yield 7.2 g of the crude product. Recrystallization from n-hexane affords 3.78 g (35%) of white crystals, [3,5-bis(1,1-dimethylethyl)-4-hydroxyphenyl] (5-chloro-1,3-dimethyl-1H-pyrazol-4-yl)methanone, mp 115.5°–117° C.; $^1$H NMR (CDCl$_3$) δ 1.45 (s, 18H, tert-butyl), 2.29 (s, 3H, C—CH$_3$), 3.85 (s, 3H, N—CH$_3$), 5.75 (s, 1H, OH), 7.68 (s, 2H, aromatics); IR (KBr) 1421, 1572, 1586, 1625, 1634 cm$^{-1}$; MS (DEI) m/e 363 (M+), 347, 157.

Anal. for $C_{20}H_{27}N_2O_2Cl$: Calcd: C, 66.20; H, 7.50; N, 7.72; Cl, 9.77. Found: C, 66.04; H, 7.48; N, 7.65; Cl, 10.21.

EXAMPLE 8

[3,5-Bis(1,1-dimethylethyl)-4-hydroxyphenyl]-1H-pyrazol-3-yl methanone

To a solution of 1-(1-pyrrolidinomethyl)-pyrazole (Katrikzky, A. R.; Rewcastle, G. W.; Fan, W-Q., J. Org. Chem., 1988, 53, 5688) (3.32 g, 0.022 mole) in THF (75 mL) at −70° C. is added 1.6M n-butyllithium (14 mL) over a 20-minute period. After stirring at that temperature 1.5 hours a solution of N-methoxy-N-methyl-[3,5-di-tert-butyl-4[(2-methoxyethoxy) methoxy] -benzamide (Example 6) (7.62 g, 0.02 mole) in THF (75 mL) is added over a 30-minute period. The reaction mixture is allowed in warm to room temperature, treated with ice-cold 2N HCl (200 mL) and concentrated to remove the THF. The concentrated mixture is extracted with CH$_2$Cl$_2$. The extracts are washed with saturated NaHCO$_3$ and brine, dried with Na$_2$SO$_4$ and evaporated. The residue is purified by flash chromatography (0–30% EtOAc/CH$_2$Cl$_2$) on silica gel to give 6.25 g of an oil. This product is deprotected by allowing to stand in 5% (w/v) HCl/MeOH (150 mL) for 2 days. The acid solution is evaporated and the residue is taken up in Et$_2$O. The resulting solution is washed with saturated NaHCO$_3$ and brine, and dried with Na$_2$SO$_4$. The ethereal solution is concentrated causing the precipitation of 3.62 g (75% of a white solid, [3,5-bis(1,1-dimethylethyl)-4-hydroxyphenyl]-1H-pyrazol-3-yl methanone, mp 216°–219° C. $^1$H NMR (DMSO-d$_6$) δ 1.42 (s, 18H, tert-butyl), 6.84 (m, 1H, OH), 8.19 (s, 2H, phenyl aromatics); pyrazole aromatics and NH appear as several poorly defined signals because of tautomerization at 7.6–7.9, 13.4, 13.9; IR (KBr) 1430, 1592, 1643 cm$^{-1}$; MS (DEI) m/e 301 (M++1), 300 (M+), 95.

Anal. for $C_{18}H_{24}N_2O_2$: Calcd: C, 71.97; H, 8.05; N, 9.33. Found: C, 71.85; H, 8.13; N, 9.22.

EXAMPLE 9

[3,5-Bis(1,1-dimethylethyl)-4-hydroxyphenyl]-1H-imidazol-2-yl methanone

To a solution of 1-[(dimethylamino)methyl]-imidazole (5.66 g, 0.0375 mole) (See Katritzky, A. R.; Rewcastle, G. W.; Fan, W-Q, J. Org. Chem. 1988, 53, 5688) in THF (100 mL) at −70° C. is added 1.6M n-butyllithium (25mL) over a 20-minute period. The mixture is stirred 1 hour and a solution of 11.83 g (0.03 mole) of N-methoxy-N-methyl-[3,5-di-tert-butyl4[(2-methoxyethoxy)methoxy]-benzamide (Example 6) in THF (75 mL) is added slowly. The reaction mixture is stirred at room temperature for 16 hours, treated with 100 mL ice-cold 2N HCl and concentrated to remove with THF. The precipitate is collected, washed with H$_2$O and dried giving 11.6 g of a white solid. A portion of this (7.7 g) is deprotected by allowing it to stand in 120 mL of 5% (w/v) HCl/MeOH for 24 hours. The acid solution is evaporated. The residue is suspended in saturated NaHCO$_3$, filtered off, washed with H$_2$O and recrystallized from MeOH to yield white crystals, [3,5-bis(1,1-dimethylethyl)-4-hydroxyphenyl]-1H-imidazol-2-yl methanone, 3.8 g (64%), mp 286°–288° C.; $^1$H NMR (DMSO-d$_6$) δ1.44 (s, 18H, tert-butyl), 7.28 (s, 1H, OH), 7.45 (broad singlet, 1H, imidazole), 7.85 (broad singlet, 1H, imidazole), 8.50 (s, 2H, phenyl), 13.22 (broad, 1H, NH); IR (Kbr) 1595, 1644, 3603 cm$^{-1}$; MS (DEI) m/e 301 (M++1), 285 (M−15).

Anal. for $C_{18}H_{24}N_2O_2$: Calcd: C, 71.97; H, 8.05; N, 9.33. Found: C, 71.95; H, 8.28; N, 9.18.

EXAMPLE 10

[3,5-Bis(1,1-dimethylethyl)-4-hydroxyphenyl)-1H-imidazol-2-yl methanone oxime

To a solution of the compound in Example 9 (1.02 g, 0.0034 mole) and 1.74 g (0.022 mole ) of pyridine in 100 mL iPrOH is added 1.18 g (0.017 mole) hydroxylamine hydrochloride. The reaction mixture is heated under reflux 24 hours and evaporated. The residue is suspended in $H_2O$ and extracted with $CH_2Cl_2$. The extracts are washed with saturated $NaHCO_3$, dried with $MgSO_4$ and evaporated. The residue is recrystallized from EtOAc yielding 0.43 g (40%) of a white solid, [3,5-bis(1,1-dimethylethyl)-4-hydroxyphenyl]-1H-imidazol-2-yl methanone oxime, mp 115°–116.5° C.; $^1H$ NMR (DMSO-$d_6$) δ 1.38 (s, 18H, tert-butyl), (iPrOH doublet at 1.04 and multiplet at 4.02), 7.31 and 7.41 (two singlets due to oxime isomers, 2H, phenyl aromatics); the imidazole aromatics, NH and OH appear as very broad and fragmented signals (6.9–7.3, 11.1, 12–12.5) totaling five protons; IR (KBr) 1420, 1440, 1460, 1500, 3350, 3610 cm$^{-1}$; MS (DEI) 316 (M++1), 298 (M-PH), 282.

Anal. for $C_{18}H_{25}N_3O_2 \cdot 0.3$ iPrOH: Calcd: C, 68.08; H, 8.28; N, 12.60. Found: C, 68.00; H, 8.14; N, 12.61.

EXAMPLE 11

[3,5-Bis(1,1-dimethylethyl)-4-hydroxyphenyl]-2-thiazolyl methanone oxime

The compound in this example is prepared from the compound in Example 4 according to the method described for Example 10. There is obtained 0.454 g white solid (55%) [3,5-bis(1,1-dimethylethyl)-4-hydroxyphenyl]-2-thiazolyl methanone oxime, mp 243°–244° C.; $^1H$ NMR (DMSO-$d_6$) δ 1.39 (s, 18H, tert-butyl), 7.19 (s, 1H, phenolic OH), 7.41 (s, 2H, phenyl aromatics), 8.03 (two overlapping doublets, 2H, imidazole aromatics), 12.8 (s, 1H, NOH); IR (KBr) 1460, 1485, 3600 cm$^{-1}$; MS (DEI) 332 (M+), 317, 302.

Anal. for $C_{18}H_{24}N_2SO_2$: Calcd: C, 65.04; H, 7.28; N, 8.43; S, 9.65. Found: C, 65.02; H, 7.21; N, 8.19; S, 9.46.

EXAMPLE 12

[3,5-Bis(1,1-dimethylethyl)-4-hydroxyphenyl](1-methyl-1H-imidazol-2-yl)methanone oxime The compound in this example is prepared from the compound in Example 3 according to the procedure described for Example 10. There is obtained 0.28 g (42%) white solid, [3,5-bis(1,1-dimethylethyl)-4-hydroxyphenyl](1-methyl-1H-imidazol-1-yl)methanone oxime, mp 284°–286° C.; $^1H$ NMR (DMSO-$d_6$) δ 1.33 (s, 18H, tert-butyl), 3.50 (s, 3H, $NCH_3$), 7.02 (s, 1H, phenolic OH), 7.25 (two singlets, 4H, aromatics), 11.6 (s, 1H, NOH); IR (KBr) 1410, 1434, 1472, 3639 cm$^{-1}$; MS (DEI) 330 (M+1), 312. (M-OH), 296.

Anal. for $C_{19}H_{27}N_3O_2$: Calcd: C, 69.27; H, 8.26; N, 12.76. Found: C, 69.24; H, 8.30; N, 12.44.

EXAMPLE 13

[3,5-Bis(1,1-dimethylethyl)-4-hydroxyphenyl]-1H-pyrazol-3-yl methanone oxime

This compound is prepared from the compound in Example 8 according to the procedure described for Example 10. There is obtained 0.49 g (39%) white solid, [3,5-bis(1,1-dimethylethyl)-4-hydroxyphenyl]-1H-pyrazol-3-yl methanone oxime, mp 156°–162° C.; $^1H$ NMR (CDCl$_3$+DMSO-$d_6$) δ 1.44 (s, 18H, tert-butyl), 5.68 (s, 1H, OH), 7.39 (s, 2H, phenyl aromatics), 6.4 and 7.4–7.6 (pyrazole aromatics, 2H, spread out as multiplet and broad signals due to tautomerism and H-bonding), 11.8–12.6 (broad, OH, NH, 2H); IR (KBr) 1420, 3620 cm$^{-1}$; MS (DEI) 315 (M+), 300.

Anal. for $C_{18}H_{25}N_3O_2 \cdot dH_2O$: Calcd: C, 67.39; H, 8.04; N, 13.10. Found: C, 67.37; H, 8.22; N, 13.11.

EXAMPLE 14

[3,5-Bis(1,1-dimethylethyl)-4-hydroxyphenyl](5-methyl-3-isoxazolyl)methanone, O-methyloxime To a mixture of [3,5-bis(1,1-dimethylethyl)-4-hydroxyphenyl(5-methyl-3-isoxazolyl)methanone (Example 1) (0.725 g, 0.0023 mole) and 1.25 g (0.015 mole) methoxylamine hydrochloride in 25 mL i-PrOH is added 1.9 g (0.024 mole) pyridine. The mixture is heated under reflux for 38 hours and evaporated and the residue is suspended in $H_2O$ and extracted with $Et_2O$. The extracts are washed with 0.2N HCl, saturated $NaHCO_3$, brine, and dried with $Na_2SO_4$. Evaporation yields an oil which is chromatographed on a Chromatotron apparatus on silica gel (1:1 $CH_2Cl_2$-n-hexane). The product fraction is evaporated and crystallized with n-pentane to give 0.17 g (22%) white crystals, 3.5-bis(1,1-dimethylethy)-4-hydroxyphenyl] (5-methyl-3-isoxazolyl)-methanone, O-methyloxime, mp 107.5°–111.5° C.; $^1H$ NMR (CDCl$_3$) δ 1.42 (s, 18H, tert-butyl), 2.48 (two singlets, 3H, C—$CH_3$), 4.0 (two singlets, 3H, $OCH_3$), 5.4 (two singlets, 1H, OH), 6.34 (two overlapping singlets, 1H, isoxazole), 7.40 (s, 2H, phenyl aromatics); IR (KBr) 1420, 1600, 3600 cm$^{-1}$; MS (DEI) 345 (M+1), 329 (M—$CH_3$), 313, 297.

Anal. for $C_{20}H_{28}N_2O_3$: Calcd: C, 69.74; H, 8.19; N, 8.13. Found: C, 69.45; H, 8.23; H, 8.06.

EXAMPLE 15

[3,5-Bis(1,1-dimethylethyl)-4-hydroxyphenyl](5-chloro-1,3-dimethyl-1H-pyrazol-4-yl)methanone oxime This compound is prepared from Example 7 according to the procedure for Example 10. There is obtained 0.75 g (53%) white crystal, [3,5-bis(1,1-dimethyethyl)-4-hydroxyphenyl](5-chloro-1,3-dimethyl-1H-pyrazol-4-yl)methanone oxime, mp>147° C.; $^1H$ NMR (CDCl$_3$) δ 1.41 (s, 18H, t-butyl), 2.13 (s, 3H, C—$CH_3$), 3.87 (s, 3H, N—$CH_3$), 5.39 (s, 1H, phenolic OH), 7.35 (s, 2H, aromatics), 8.70 (s, 1H, N—OH); IR (KBr) 1438, 1541, 3631 cm$^{-1}$; MS (EI) 379 (M+1), 378 (M+), 377 (M-1), 362 (M-16), 191.

Anal. for $C_{20}H_{28}N_3O_2Cl$: Calcd: C, 63.56; H, 7.47; N, 11.12; Cl, 9.38. Found: C, 63.16; H, 7.43; N, 11.02; C., 9.52.

EXAMPLE 16

[3,5-Bis(1,1-dimethylethyl)-4-hydroxyphenyl]-2-oxazolyl methanone

This compound is prepared from oxazole using the method described in Example 8. There is obtained 0.378 g (11%) white crystals, mp 127°–130° C.; $^1H$ NMR (CDCl$_3$) δ 1.50 (s, 18H, tert-butyl), 5.87 (s, 1H, OH), 7.40 (s, 1H, oxazole), 7.87 (s, 1H, oxazole), 8.45 (s, 2H, phenyl); IR(KBr) 1647, 3593 cm$^{-1}$; MS (EI) 301 (M+), 287, 286, 217.

Anal. for $C_{18}H_{23}NO_3$: Calcd: C, 71.73; H, 7.69; N, 4.65. Found: C, 72.08; H, 7.81; N, 4.00.

EXAMPLE 17

2-[]3,5-Bis(1,1-dimethylethyl)-4-hydroxyphenyl]-carbonyl]-1H-imidazole-5-carboxylic acid monohydrochloride To a solution of 1-[(dimethylamino)methyl]-imidazole (Katritzky, A. R. Rewcastle, G. W. Fan, W-Q., J. Org. Chem. 1988, 53, 5688 (3.02 g, 0.02 mole) in THF (75 mL) at −78° is added 1.6M n-butyllithium (14 mL, 0.022 mole). The mixture is warmed at 0° C. for 20 minutes and cooled to −78° C. and a solution of N-methoxy-N-methyl-[3,5-di-tert-butyl-4[(2-methoxyethoxy)methoxy]]benzamide (Example 6) in THF (50 mL) is added slowly. After stirring at room temperature 17 hours and recooling to −78° C., 1.7M tert-butyllithium (13 mL, 0.022 mole) is added. The mixture is allowed to come to −10° C. and then is recooled to −78° C. Several chunks of solid $CO_2$ are added and the reaction mixture is allowed to come to room temperature and 1N HCl (100 mL) is added. The THF is removed by concentrating and the mixture is extracted with $CH_2Cl_2$. The extracts are washed with brine and dried with $Na_2SO_4$ and evaporated. The crude produce is deprotected by allowing it to stand in 5% (w/v) HCl/MeOH (100 mL) for 50 hours. This solution is evaporated and the residue is crystallized in 20% (w/v) HCl/$Et_2O$ to yield a yellow solid, 1.92 g (25%), mp >172° C.; $^1$H NMR (DMSO-$d_6$) δ 1.44 (s, 18H, tert-butyl), 7.99 (s, 2H, aromatics), 8.49 (b, 2H, aromatic+OH), 8.6–11.0 (broad, 2H, exchangeable); IR(KBr) 1590, 1630, 1660, 1730 (broad), 3609 cm$^{-1}$; MS (EI) 344 (M+), 329 (M−15), 311, 300 (M−$CO_2$).

Anal. for $C_{19}H_{24}N_2O_4$·HCl: Calcd: C, 59.92; H, 6.62; N, 7.36; Cl$^-$, 9.31. Found: C, 59.89; H, 6.83; N, 7.16; Cl$^-$, 8.97.

EXAMPLE 18

[3,5-Bis(1,1)dimethylethyl)-4-hydroxyphenyl]-2-thiazolylmethanone, O-methyloxime This compound is prepared from the compound in Example 4 according to the method described for Example 14. There is obtained 0.877 g (54%) white crystals, mp 113°–115° C.; $^1$H NMR 1.44 (two singlets, 18H, tert-butyl of each oxime isomer), 4.05 and 4.22 (2s, 3H, $OCH_3$), 5.37 and 5.45 (2s, 1H, OH), 7.31–8.00 (m, 4H, aromatics); IR(KBr) 1060, 3555, 3588 cm$^{-1}$; MS (EI) 346 (M+), 331 (M−$CH_3$), 315 (M−$OCH_3$), 299.

Anal. for $C_{19}H_{26}N_2O_2S$: Calcd: C, 65.87; H, 7.57; N, 8.09; S, 9.26. Found: C, 66.21; H, 7.81; N, 8.06; S, 9.16.

EXAMPLE 19

[3,5-Bis(1,1-dimethylethyl)-4-hydroxyphenyl](1H-pyrazol-3-yl methanone O-methyloxime (2:1 mixture of isomers)

This compound is prepared from the compound in Example 8 according to the method described for Example 14. There is obtained 0.033 g (6%) white crystals, mp 192°–194° C.; $^1$H NMR (CDCl$_3$) 1.35 (s, 18H, tert-butyl), 3.9 (two singlets, 3H, $CH_3$ oxime isomers), 6.3–7.8 (m, 5H, 4 aromatic+OH), 13.2 (two singlets, 1H, NH); IR(KBr) 1430, 1520, 3660 cm$^{-1}$; MS (EI) 329 (M+), 314 (M−15), 298.

Anal. for $C_{19}H_{27}N_3O_2$: Calcd: C, 69.27; H, 8.26; N, 12.75. Found: C, 69.29; H, 8.26; N, 12.61.

EXAMPLE 20

[3,5-Bis(1,1-dimethylethyl)-4-hydroxyphenyl]-(5-chloro-1,3-dimethyl-1H-pyrazol-4-yl)methanone, O-methyloxime This compound is prepared from the compound in Example 7 according to the method described for Example 14. There is obtained 0.403 g (42%) yellow crystals, mp 120°–122° C.; $^1$H NMR (DMSO-$d_6$) δ 1.41 (s,18H, tert-butyl), 2.06 (s, 3H, methyl), 3.83 (s, 3H, $NCH_3$), 4.00 (s, 3H, $OCH_3$), 5.37 (s, 1H, OH), 7.33 (s, 2H, aromatics); IR(KBr) 1550, 1620, 3500 (broad) cm$^{-1}$; MS (EI) 391 (M+), 376 (M−$CH_3$), 360 (M−$OCH_3$), 344.

Anal. for $C_{21}H_{30}N_3O_2Cl$: Calcd: C, 64.35; H, 7.72; N, 10.72; Cl, 9.05. Found: C, 64.45; H, 7.87; N, 10.65; Cl, 9.14.

[3,5-Bis(1,1-dimethylethyl)-4-hydroxyphenyl]-2-oxazolyl methanone oxime (single unknown oxime isomer)

This compound is prepared from the compound in Example 16 according to the method for Example 10. There is obtained 0.297 g (57%) white crystals, mp 245°–248° C.; $^1$H NMR (DMSO-$d_6$) δ 1.37 (s, 18H, tert-butyl), 7.31 (m, 4H, aromatics), 8.18 (s, 1H, OH), 11.90 (S, 1H, NOH); IR(KBr) 1550, 1633, 1653, 3622 cm$^{-1}$; MS (EI) 316 (M+), 301, 286, 283.

Anal. for $C_{18}H_{24}N_2O_3$: Calcd: C, 68.33; H, 7.65; N, 8.85. Found: C, 67.95; H, 7.50; N, 8.74.

EXAMPLE 22

[3,5-Bis(1,1-dimethylethyl)-4-hydroxyphenyl]-2-oxazolyl methanone, O-methyloxime (4:1 mixture of oxime isomers)

This compound is prepared from the compound in Example 16 according to the method described for Example 14. This is obtained 0.360 g (68%) white crystals, mp 127°–132° C.; $^1$H NMR (CDDl$_3$) δ 1.44 (two singlets, 18H, tert-butyl (2 oxime isomers present)), 4.09 (s, 3H, $CH_3$), 5.42 and 5.47 (two singlets, 1H, OH), 7.26–7.79 (m, 4H, aromatics); IR(KBr) 1440, 3150, 3600 cm$^{-1}$; MS (EI) 330 (M+), 315 (M−$CH_3$), 299 (M−$OCH_3$).

Anal. for $C_{19}H_{26}N_2O_3$: Calcd: C, 69.06; H, 7.93; N, 8.48. Found: C, 69.40; H, 8.06; N, 8.56.

EXAMPLE 23

2-[[3,5-Bis(1,1-dimethylethyl)-4-hydroxyphenyl]-(hydroxyimino)methyl]-1H-imidazole-5-carboxylic acid (mixture of isomers)

To a solution of the compound in Example 17 (0.50 g, 0.0013 mole) and 1.47 g (0.0185 mole) pyridine in 35 mL iPrOH is added 0.452 g (0.0065 mole) hydroxylamine hydrochloride. The reaction mixture is heated under reflux 48 hours and is evaporated. The residue is taken up in $Et_2O$ and washed twice with $H_2O$ containing enough HOAc to bring pH to 4 and once with brine. After drying with $MgSO_4$ and evaporating the solvent the residue is recrystallized from $Et_2O$-n-hexane to yield 0.22 g white solid (47%), mp >168° C.; $^1$H NMR (DMSO-$d_6$+CDCl$_3$) 1.44 (s, 18H, tert-butyl), 5.57 (broad, 1H), 7.19–7.78 (m, 4H, 3 aromatics+1 exchangeable), 11.6–12.3 (broad, 1H); IR(KBr) 1701, 3630 cm$^{-1}$; MS (EI) 359 (M−), 344, 315 (M−$CO_2$).

Anal. for $C_{19}H_{25}N_3O_4 \cdot 0.3H_2O$: Calcd: C, 62.55; H, 7.07; N, 11.52; $H_2O$, 1.64. Found: C, 62.90; H, 7.14; N, 11.27; $H_2O$, 1.93.

EXAMPLE 24

[3,5-Bis(1,1-dimethylethyl)-4-hydroxyphenyl](1-methyl-1H-imidazol-2-yl) methanone, O-methyloxime To a mixture of [3,5-bis(1,1-dimethylethyl)-4-hydroxyphenyl]-1H-imidazol-2-yl methanone (Example 9) (0.41 g, 1.36 mmole) and 0.55 g (6.6 mmole) methoxylamine hydrochloride in 35 mL i-PrOH is added 0.8 g (10.0 mmole) pyridine. The mixture is heated under reflux 48 hours and evaporated and the residue is taken up in $CH_2Cl_2$ and washed with 1N HCl, two times with saturated $NaHCO_3$ and dried with $Na_2SO_4$ and evaporated. The residue is recrystallized from $Et_2O$-n-hexane yielding 0.305 g (63%) of white crystals, mp 222°–223° C.; $^1$H NMR ($CDCl_3$) δ 1.44 (s, 18H, tert-butyl), 3.98 and 4.16 (two singlets, 3H, $OCH_3$ oxime isomers), 5.3 and 5.4 (two singlets, 1H, OH), 7.0–7.5 (m, 4H, aromatics), 0.8–1.3 (m, 4.6H, n-hexane); IR(KBr) 1040, 1450, 3600 $cm^{-1}$; MS (EI) 329 (M+), 314 (M—$CH_3$), 298 (M—$OCH_3$), 282.

Anal. for $C_{19}H_{27}N_3O_2 \cdot 0.33C_6H_{14}$: Calcd: C, 70.42; H, 8.91; N, 11.73. Found: C, 70.40; H, 8.87; N, 11.55.

EXAMPLE 25

[3,5-Bis(1,1-dimethylethyl)-4-hydroxyphenyl]-(1-methyl-1H-imidazol-2-yl)methanone, O-methyloxime This compound is prepared from the compound in Example 3 according to the method for Example 14. There is obtained 0.03 g (13%) white crystals, mp 122°–127° C.; $^1$H NMR ($CDCl_3$) δ 1.39 (s, 18H, tert-butyl), 3.57 (s, 3H, $NCH_3$), 4.00 (s, 3H, $OCH_3$), 5.39 (s, 1H, OH), 6.99 (s, 1H, imidazole), 7.17 (s, 1H, imidazole), 7.31 (s, 2H, phenyl); IR(KBr) 1435, 1464 $cm^{-1}$; MS (EI) 344, 343 (M+), 328, 312, 301, 296.

Anal. for $C_{20}H_{29}N_3O_2$: Calcd: C, 69.94; H, 8.51; N, 12.23. Found: C, 69.68; H, 8.34; N, 11.93.

We claim:

1. A compound of the formula

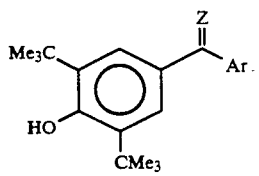

and a pharmaceutically acceptable base or acid addition salt thereof; wherein

Z is O, NOH, or $NOCH_3$;

Ar is

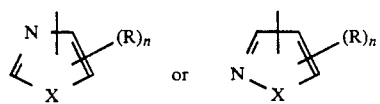

wherein

X is S;

R is hydrogen, lower alkyl, halogen, $CO_2R_2$ or

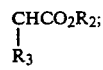

wherein $R_1$ is hydrogen or lower alkyl; and $R_2$ and $R_3$ are independently hydrogen or lower alkyl; and n is an integer of one or two with the proviso that when n is two then R cannot be $CO_2R_2$ or

2. A compound of claim 1 wherein X is S and R, $R_2$, $R_3$, and Z are as defined above.

3. A compound of claim 1 wherein Z is O and Ar is as defined above.

4. A compound of claim 1 wherein Z is NOH and Ar is as defined above.

5. A compound of claim 1 wherein Z is $NOCH_3$ and Ar is as defined above.

6. A compound of claim 1 which is [3,5-bis(1,1-dimethylethyl)-4-hydroxyphenyl]-2-thiazolylmethanone.

7. A compound of claim 1 which is [3,5-bis(1,1-dimethylethyl)-4-hydroxyphenyl]-2-thiazolylmethanone oxime.

8. A compound of claim 1 which is [3,5-bis(1,1-dimethylethyl)-4-hydroxyphenyl]-2-thiazolylmethanone, O-methyloxime.

9. A pharmaceutical composition for use as an inhibitor of 5-lipoxygenase, cyclooxygenase, or both comprising a 5-lipoxygenase, cyclooxygenase or both inhibiting amount of a compound of claim 1 and a pharmaceutically acceptable carrier.

10. A method for treating an inflammatory disease or condition in a human suffering therefrom which comprises administering a compound of claim 1 in unit dosage form.

11. A pharmaceutical composition which comprises a compound of the claim 1 and a nonsteroidal antiinflammatory agent in a weight ratio of from 1000 to 1 to 1 to 1000.

* * * * *

UNITED STATES PATENT AND TRADEMARK OFFICE
CERTIFICATE OF CORRECTION

PATENT NO. : 5,086,064

DATED : February 4, 1992

INVENTOR(S) : Capiris, et al

It is certified that error appears in the above-identified patent and that said Letters Patent is hereby corrected as shown below:

At Column 20, line 19, insert "EXAMPLE 21" before the title which starts on line 20.

In column 21, line 29, delete at the end of the line "(1-meth-".

In column 21, line 30, delete at the beginning of the line "yl-".

Signed and Sealed this

Tenth Day of August, 1993

Attest:

MICHAEL K. KIRK

Attesting Officer

Acting Commissioner of Patents and Trademarks